US007384636B2

(12) United States Patent
Nishizawa

(10) Patent No.: US 7,384,636 B2
(45) Date of Patent: Jun. 10, 2008

(54) POLYPEPTIDE

(75) Inventor: Toshiki Nishizawa, Tokyo (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 10/551,692

(22) PCT Filed: Mar. 29, 2004

(86) PCT No.: PCT/JP2004/004460

§ 371 (c)(1), (2), (4) Date: Sep. 30, 2005

(87) PCT Pub. No.: WO2004/087767

PCT Pub. Date: Oct. 14, 2004

(65) Prior Publication Data

US 2007/0020257 A1 Jan. 25, 2007

(30) Foreign Application Priority Data

Mar. 31, 2003 (JP) ............................ 2003-093243

(51) Int. Cl.
*A61K 38/02* (2006.01)
*A61K 39/00* (2006.01)

(52) U.S. Cl. .................................... 424/185.1; 530/324

(58) Field of Classification Search ..................... None
See application file for complete search history.

(56) References Cited

FOREIGN PATENT DOCUMENTS

| | | | |
|---|---|---|---|
| FR | 2 776 926 | * | 4/1998 |
| WO | WO 01/81426 A2 | | 11/2001 |

OTHER PUBLICATIONS

Maier et al. Short amyloid-beta (Abeta) immunogens reduce cerebral Abeta load and learning deficits in an Alzheimer's disease mouse model in the absence of an Abeta-specific cellular immune response. J Neurosci. May 3, 2006;26(18):4717-28.*

Okada et al. Efficient antigen gene transduction using Arg-Gly-Asp fiber-mutant adenovirus vectors can potentiate antitumor vaccine efficacy and maturation of murine dendritic cells. Cancer Res. Nov. 1, 2001;61(21):7913-9.*

Akira Yano et al., "An ingenious design for peptide vaccines", *Vaccine*, vol. 23, pp. 2322-2326, Mar. 18, 2005.

Akira Yano et al., "RGD motif enhances immunogenicity and adjuvanicity of peptide antigens following antranasal immunization", *Vaccine*, vol. 222, pp. 237-243, Dec. 12, 2003.

Q. Zhang et al., "Immunogenicity of a recombinant fusion protein of tandem repeat epitopes of foot-and-mouth disease virus type Asia 1 for guinea pigs", *Acta Virologica*, vol. 46, pp. 1-9, 2002.

Oishi Y. Onozuka et al., "The effect of amino acid spacers on the antigenicity of dimeric peptide-inducing cross-reacting antibodies to a cell surface protein antigen of *Streptococcus mutans", Oral Microbiology and Immunology*, vol. 16, No. 1, pp. 40-44, Feb. 2001.

* cited by examiner

*Primary Examiner*—Maher M. Haddad
(74) *Attorney, Agent, or Firm*—Browdy and Neimark, PLLC

(57) ABSTRACT

The present invention provides a polypeptide inducing the production of an antibody in permucosal administration in the presence of no immunological adjuvant, a composition containing the polypeptide, and use thereof. The present invention solves the above object by providing a polypeptide inserted with a cell attachment motif of a cell adhesive molecule to the peptide which has an amino acid sequence of multiagretope type T cell epitope at the amino terminal side of an inserted linker peptide, and an amino acid sequence of a B cell epitope at the carboxyl terminal side of the inserted linker peptide, a composition containing the polypeptide, and use thereof.

2 Claims, No Drawings

```
                         SEQUENCE LISTING

<160> NUMBER OF SEQ ID NOS: 47

<210> SEQ ID NO 1
<211> LENGTH: 13
<212> TYPE: PRT
<213> ORGANISM: Artificial Sequence
<220> FEATURE:
<223> OTHER INFORMATION: Peptide fragment of PAc at the positions of 365
      to 377

<400> SEQUENCE: 1

Thr Tyr Glu Ala Ala Leu Lys Gln Tyr Glu Ala Asp Leu
  1               5                  10


<210> SEQ ID NO 2
<211> LENGTH: 3
<212> TYPE: PRT
<213> ORGANISM: Artificial Sequence
<220> FEATURE:
<223> OTHER INFORMATION: Integrin binding motif

<400> SEQUENCE: 2

Arg Gly Asp
  1


<210> SEQ ID NO 3
<211> LENGTH: 3
<212> TYPE: PRT
<213> ORGANISM: Artificial Sequence
<220> FEATURE:
<223> OTHER INFORMATION: Integrin binding motif

<400> SEQUENCE: 3

Arg Glu Asp
```

-continued

```
  1


<210> SEQ ID NO 4
<211> LENGTH: 3
<212> TYPE: PRT
<213> ORGANISM: Artificial Sequence
<220> FEATURE:
<223> OTHER INFORMATION: Integrin binding motif

<400> SEQUENCE: 4

Leu Asp Val
  1


<210> SEQ ID NO 5
<211> LENGTH: 5
<212> TYPE: PRT
<213> ORGANISM: Artificial Sequence
<220> FEATURE:
<223> OTHER INFORMATION: Integrin binding motif

<400> SEQUENCE: 5

Pro His Ser Arg Asn
  1               5


<210> SEQ ID NO 6
<211> LENGTH: 3
<212> TYPE: PRT
<213> ORGANISM: Artificial Sequence
<220> FEATURE:
<223> OTHER INFORMATION: Integrin binding motif

<400> SEQUENCE: 6

Arg Lys Lys
  1


<210> SEQ ID NO 7
<211> LENGTH: 4
<212> TYPE: PRT
<213> ORGANISM: Artificial Sequence
<220> FEATURE:
<223> OTHER INFORMATION: Integrin binding motif

<400> SEQUENCE: 7

Asp Gly Glu Ala
  1


<210> SEQ ID NO 8
<211> LENGTH: 5
<212> TYPE: PRT
<213> ORGANISM: Artificial Sequence
<220> FEATURE:
<223> OTHER INFORMATION: Integrin binding motif

<400> SEQUENCE: 8

Tyr Ile Gly Ser Arg
  1               5


<210> SEQ ID NO 9
<211> LENGTH: 5
<212> TYPE: PRT
<213> ORGANISM: Artificial Sequence
<220> FEATURE:
<223> OTHER INFORMATION: Integrin binding motif

<400> SEQUENCE: 9

Ile Lys Val Ala Val
  1               5
```

-continued

<210> SEQ ID NO 10
<211> LENGTH: 8
<212> TYPE: PRT
<213> ORGANISM: Artificial Sequence
<220> FEATURE:
<223> OTHER INFORMATION: Integrin binding motif

<400> SEQUENCE: 10

Arg Phe Tyr Val Val Met Trp Lys
1 5

<210> SEQ ID NO 11
<211> LENGTH: 5
<212> TYPE: PRT
<213> ORGANISM: Artificial Sequence
<220> FEATURE:
<223> OTHER INFORMATION: Integrin binding motif

<400> SEQUENCE: 11

Ile Arg Val Val Met
1 5

<210> SEQ ID NO 12
<211> LENGTH: 13
<212> TYPE: PRT
<213> ORGANISM: Artificial Sequence
<220> FEATURE:
<223> OTHER INFORMATION: A mutated unit peptide

<400> SEQUENCE: 12

Thr Tyr Glu Ala Ala Leu Lys Gln Tyr Gln Thr Glu Leu
1 5 10

<210> SEQ ID NO 13
<211> LENGTH: 13
<212> TYPE: PRT
<213> ORGANISM: Artificial Sequence
<220> FEATURE:
<223> OTHER INFORMATION: A mutated unit peptide

<400> SEQUENCE: 13

Thr Tyr Glu Ala Ala Leu Lys Gln Tyr Glu Thr Asp Leu
1 5 10

<210> SEQ ID NO 14
<211> LENGTH: 13
<212> TYPE: PRT
<213> ORGANISM: Artificial Sequence
<220> FEATURE:
<223> OTHER INFORMATION: A mutated unit peptide

<400> SEQUENCE: 14

Thr Tyr Glu Ala Ala Leu Lys Gln Tyr Glu Thr Ala Leu
1 5 10

<210> SEQ ID NO 15
<211> LENGTH: 16
<212> TYPE: PRT
<213> ORGANISM: Artificial Sequence
<220> FEATURE:
<223> OTHER INFORMATION: A mutated unit peptide

<400> SEQUENCE: 15

Thr Tyr Glu Ala Ala Leu Lys Gln Tyr Glu Ala Asp Leu Lys Gln Tyr
1 5 10 15

-continued

<210> SEQ ID NO 16
<211> LENGTH: 14
<212> TYPE: PRT
<213> ORGANISM: Artificial Sequence
<220> FEATURE:
<223> OTHER INFORMATION: A mutated unit peptide

<400> SEQUENCE: 16

```
Asn Glu Ala Asp Tyr Gln Ala Lys Leu Thr Ala Tyr Gln Thr
  1               5                  10
```

<210> SEQ ID NO 17
<211> LENGTH: 27
<212> TYPE: PRT
<213> ORGANISM: Artificial Sequence
<220> FEATURE:
<223> OTHER INFORMATION: Unit peptide - PAc(305-318)

<400> SEQUENCE: 17

```
Thr Tyr Glu Ala Ala Leu Lys Gln Tyr Glu Ala Asp Leu Asn Glu Ala
  1               5                  10                  15

Asp Tyr Gln Ala Lys Leu Thr Ala Tyr Gln Thr
             20                  25
```

<210> SEQ ID NO 18
<211> LENGTH: 27
<212> TYPE: PRT
<213> ORGANISM: Artificial Sequence
<220> FEATURE:
<223> OTHER INFORMATION: PAc(305-318) fragment - unit peptide

<400> SEQUENCE: 18

```
Asn Glu Ala Asp Tyr Gln Ala Lys Leu Thr Ala Tyr Gln Thr Thr Tyr
  1               5                  10                  15

Glu Ala Ala Leu Lys Gln Tyr Glu Ala Asp Leu
             20                  25
```

<210> SEQ ID NO 19
<211> LENGTH: 20
<212> TYPE: PRT
<213> ORGANISM: Artificial Sequence
<220> FEATURE:
<223> OTHER INFORMATION: OMP

<400> SEQUENCE: 19

```
Leu Ala Val Tyr Trp Glu Leu Leu Ala Lys Tyr Leu Leu Asp Arg Val
  1               5                  10                  15

Gln Lys Val Ala
             20
```

<210> SEQ ID NO 20
<211> LENGTH: 35
<212> TYPE: PRT
<213> ORGANISM: Artificial Sequence
<220> FEATURE:
<223> OTHER INFORMATION: OMP-KK-UP

<400> SEQUENCE: 20

```
Leu Ala Val Tyr Trp Glu Leu Leu Ala Lys Tyr Leu Leu Asp Arg Val
  1               5                  10                  15

Gln Lys Val Ala Lys Lys Thr Tyr Glu Ala Ala Leu Lys Gln Tyr Glu
             20                  25                  30

Ala Asp Leu
         35
```

-continued

<210> SEQ ID NO 21
<211> LENGTH: 35
<212> TYPE: PRT
<213> ORGANISM: Artificial Sequence
<220> FEATURE:
<223> OTHER INFORMATION: UP-KK-OMP

<400> SEQUENCE: 21

```
Thr Tyr Glu Ala Ala Leu Lys Gln Tyr Glu Ala Asp Leu Lys Lys Leu
  1               5                  10                  15

Ala Val Tyr Trp Glu Leu Leu Ala Lys Tyr Leu Leu Asp Arg Val Gln
             20                  25                  30

Lys Val Ala
         35
```

<210> SEQ ID NO 22
<211> LENGTH: 28
<212> TYPE: PRT
<213> ORGANISM: Artificial Sequence
<220> FEATURE:
<223> OTHER INFORMATION: Di unit peptide (UP-KK-UP)

<400> SEQUENCE: 22

```
Thr Tyr Glu Ala Ala Leu Lys Gln Tyr Glu Ala Asp Leu Lys Lys Thr
  1               5                  10                  15

Tyr Glu Ala Ala Leu Lys Gln Tyr Glu Ala Asp Leu
             20                  25
```

<210> SEQ ID NO 23
<211> LENGTH: 3
<212> TYPE: PRT
<213> ORGANISM: Artificial Sequence
<220> FEATURE:
<223> OTHER INFORMATION: Cadherin binding motif

<400> SEQUENCE: 23

```
Asp Arg Glu
  1
```

<210> SEQ ID NO 24
<211> LENGTH: 3
<212> TYPE: PRT
<213> ORGANISM: Artificial Sequence
<220> FEATURE:
<223> OTHER INFORMATION: Cadherin binding motif

<400> SEQUENCE: 24

```
Asp Glu Asp
  1
```

<210> SEQ ID NO 25
<211> LENGTH: 3
<212> TYPE: PRT
<213> ORGANISM: Artificial Sequence
<220> FEATURE:
<223> OTHER INFORMATION: Cadherin binding motif

<400> SEQUENCE: 25

```
His Ala Val
  1
```

<210> SEQ ID NO 26
<211> LENGTH: 4
<212> TYPE: PRT

-continued

```
<213> ORGANISM: Artificial Sequence
<220> FEATURE:
<223> OTHER INFORMATION: Cadherin binding motif

<400> SEQUENCE: 26

Arg Gly Asp Ser
  1


<210> SEQ ID NO 27
<211> LENGTH: 31
<212> TYPE: PRT
<213> ORGANISM: Artificial Sequence
<220> FEATURE:
<223> OTHER INFORMATION: RGD-di unit peptide (DUP)

<400> SEQUENCE: 27

Arg Gly Asp Thr Tyr Glu Ala Ala Leu Lys Gln Tyr Glu Ala Asp Leu
  1               5                  10                  15

Lys Lys Thr Tyr Glu Ala Ala Leu Lys Gln Tyr Glu Ala Asp Leu
             20                  25                  30


<210> SEQ ID NO 28
<211> LENGTH: 31
<212> TYPE: PRT
<213> ORGANISM: Artificial Sequence
<220> FEATURE:
<223> OTHER INFORMATION: RED-di unit peptide (DUP)

<400> SEQUENCE: 28

Arg Glu Asp Thr Tyr Glu Ala Ala Leu Lys Gln Tyr Glu Ala Asp Leu
  1               5                  10                  15

Lys Lys Thr Tyr Glu Ala Ala Leu Lys Gln Tyr Glu Ala Asp Leu
             20                  25                  30


<210> SEQ ID NO 29
<211> LENGTH: 33
<212> TYPE: PRT
<213> ORGANISM: Artificial Sequence
<220> FEATURE:
<223> OTHER INFORMATION: YIGSR-di unit peptide (DUP)

<400> SEQUENCE: 29

Tyr Ile Gly Ser Arg Thr Tyr Glu Ala Ala Leu Lys Gln Tyr Glu Ala
  1               5                  10                  15

Asp Leu Lys Lys Thr Tyr Glu Ala Ala Leu Lys Gln Tyr Glu Ala Asp
             20                  25                  30

Leu


<210> SEQ ID NO 30
<211> LENGTH: 31
<212> TYPE: PRT
<213> ORGANISM: Artificial Sequence
<220> FEATURE:
<223> OTHER INFORMATION: DED-di unit peptide (DUP)

<400> SEQUENCE: 30

Asp Glu Asp Thr Tyr Glu Ala Ala Leu Lys Gln Tyr Glu Ala Asp Leu
  1               5                  10                  15

Lys Lys Thr Tyr Glu Ala Ala Leu Lys Gln Tyr Glu Ala Asp Leu
             20                  25                  30


<210> SEQ ID NO 31
<211> LENGTH: 31
<212> TYPE: PRT
```

-continued

<213> ORGANISM: Artificial Sequence
<220> FEATURE:
<223> OTHER INFORMATION: HAV-di unit peptide (DUP)

<400> SEQUENCE: 31

His Ala Val Thr Tyr Glu Ala Ala Leu Lys Gln Tyr Glu Ala Asp Leu
1 5 10 15

Lys Lys Thr Tyr Glu Ala Ala Leu Lys Gln Tyr Glu Ala Asp Leu
20 25 30

<210> SEQ ID NO 32
<211> LENGTH: 38
<212> TYPE: PRT
<213> ORGANISM: Artificial Sequence
<220> FEATURE:
<223> OTHER INFORMATION: RGD-OMP-KK-UP

<400> SEQUENCE: 32

Arg Gly Asp Leu Ala Val Tyr Trp Glu Leu Leu Ala Lys Tyr Leu Leu
1 5 10 15

Asp Arg Val Gln Lys Val Ala Lys Lys Thr Tyr Glu Ala Ala Leu Lys
20 25 30

Gln Tyr Glu Ala Asp Leu
35

<210> SEQ ID NO 33
<211> LENGTH: 38
<212> TYPE: PRT
<213> ORGANISM: Artificial Sequence
<220> FEATURE:
<223> OTHER INFORMATION: OMP-RGD-KK-UP

<400> SEQUENCE: 33

Leu Ala Val Tyr Trp Glu Leu Leu Ala Lys Tyr Leu Leu Asp Arg Val
1 5 10 15

Gln Lys Val Ala Arg Gly Asp Lys Lys Thr Tyr Glu Ala Ala Leu Lys
20 25 30

Gln Tyr Glu Ala Asp Leu
35

<210> SEQ ID NO 34
<211> LENGTH: 38
<212> TYPE: PRT
<213> ORGANISM: Artificial Sequence
<220> FEATURE:
<223> OTHER INFORMATION: OMP-KK-RGD-UP

<400> SEQUENCE: 34

Leu Ala Val Tyr Trp Glu Leu Leu Ala Lys Tyr Leu Leu Asp Arg Val
1 5 10 15

Gln Lys Val Ala Lys Lys Arg Gly Asp Thr Tyr Glu Ala Ala Leu Lys
20 25 30

Gln Tyr Glu Ala Asp Leu
35

<210> SEQ ID NO 35
<211> LENGTH: 38
<212> TYPE: PRT
<213> ORGANISM: Artificial Sequence
<220> FEATURE:
<223> OTHER INFORMATION: RGD-KK-UP-RGD

<400> SEQUENCE: 35

-continued

Leu Ala Val Tyr Trp Glu Leu Leu Ala Lys Tyr Leu Leu Asp Arg Val
1 5 10 15

Gln Lys Val Ala Lys Lys Thr Tyr Glu Ala Ala Leu Lys Gln Tyr Glu
20 25 30

Ala Asp Leu Arg Gly Asp
35

<210> SEQ ID NO 36
<211> LENGTH: 16
<212> TYPE: PRT
<213> ORGANISM: Artificial Sequence
<220> FEATURE:
<223> OTHER INFORMATION: T1 peptide derived from HIV IIIB gp120

<400> SEQUENCE: 36

Lys Gln Ile Ile Asn Met Trp Gln Ala Val Gly Lys Ala Met Tyr Ala
1 5 10 15

<210> SEQ ID NO 37
<211> LENGTH: 14
<212> TYPE: PRT
<213> ORGANISM: Artificial Sequence
<220> FEATURE:
<223> OTHER INFORMATION: OVAp derived from ovalbumin

<400> SEQUENCE: 37

Ile Ser Gln Ala Val His Ala Ala His Ala Glu Ile Asn Glu
1 5 10

<210> SEQ ID NO 38
<211> LENGTH: 39
<212> TYPE: PRT
<213> ORGANISM: Artificial Sequence
<220> FEATURE:
<223> OTHER INFORMATION: RGD-OMP-KK-UP

<400> SEQUENCE: 38

Arg Gly Asp Leu Ala Val Tyr Trp Glu Leu Leu Ala Lys Tyr Leu Leu
1 5 10 15

Asp Arg Val Gln Lys Val Ala Lys Lys Ile Ser Gln Ala Val His Ala
20 25 30

Ala His Ala Glu Ile Asn Glu
35

<210> SEQ ID NO 39
<211> LENGTH: 34
<212> TYPE: PRT
<213> ORGANISM: Artificial Sequence
<220> FEATURE:
<223> OTHER INFORMATION: T1-RGD-KK-UP

<400> SEQUENCE: 39

Lys Gln Ile Ile Asn Met Trp Gln Ala Val Gly Lys Ala Met Tyr Ala
1 5 10 15

Arg Gly Asp Lys Lys Thr Tyr Glu Ala Ala Leu Lys Gln Tyr Glu Ala
20 25 30

Asp Leu

<210> SEQ ID NO 40
<211> LENGTH: 36
<212> TYPE: PRT
<213> ORGANISM: Artificial Sequence
<220> FEATURE:
<223> OTHER INFORMATION: OMP-KK-OVAp -continued

<400> SEQUENCE: 40

Leu Ala Val Tyr Trp Glu Leu Leu Ala Lys Tyr Leu Leu Asp Arg Val
1               5                   10                  15

Gln Lys Val Ala Lys Lys Ile Ser Gln Ala Val His Ala Ala His Ala
            20                  25                  30

Glu Ile Asn Glu
        35

<210> SEQ ID NO 41
<211> LENGTH: 31
<212> TYPE: PRT
<213> ORGANISM: Artificial Sequence
<220> FEATURE:
<223> OTHER INFORMATION: T1-KK-UP

<400> SEQUENCE: 41

Lys Gln Ile Ile Asn Met Trp Gln Ala Val Gly Lys Ala Met Tyr Ala
1               5                   10                  15

Lys Lys Thr Tyr Glu Ala Ala Leu Lys Gln Tyr Glu Ala Asp Leu
            20                  25                  30

<210> SEQ ID NO 42
<211> LENGTH: 15
<212> TYPE: PRT
<213> ORGANISM: Artificial Sequence
<220> FEATURE:
<223> OTHER INFORMATION: gag protein at the position of 298-312

<400> SEQUENCE: 42

Lys Arg Trp Ile Ile Leu Gly Leu Asn Lys Ile Val Arg Met Tyr
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: pol protein at the position of 596-610

<400> SEQUENCE: 43

Trp Glu Phe Val Asn Thr Pro Pro Leu Val Lys Leu Trp Tyr Gln
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: V3 loop peptide of gp120 protein from HIV

<400> SEQUENCE: 44

Lys Arg Lys Arg Ile His Gly Pro Gly Arg Ala Phe Tyr Thr Thr Lys
1               5                   10                  15

<210> SEQ ID NO 45
<211> LENGTH: 18
<212> TYPE: PRT
<213> ORGANISM: Artificial Sequence
<220> FEATURE:
<223> OTHER INFORMATION: HA (hemaggrutinin) protein at the position of
      91-108 from influenza virus

<400> SEQUENCE: 45

Ser Lys Ala Phe Ser Asn Cys Tyr Pro Tyr Asp Val Pro Asp Tyr Ala

-continued

```
  1               5                   10                  15

Ser Leu


<210> SEQ ID NO 46
<211> LENGTH: 13
<212> TYPE: PRT
<213> ORGANISM: Artificial Sequence
<220> FEATURE:
<223> OTHER INFORMATION: L2 protein from human papilloma

<400> SEQUENCE: 46

Leu Val Glu Glu Thr Ser Phe Ile Asp Ala Gly Ala Pro
  1               5                   10


<210> SEQ ID NO 47
<211> LENGTH: 16
<212> TYPE: PRT
<213> ORGANISM: Artificial Sequence
<220> FEATURE:
<223> OTHER INFORMATION: A polypeptide for treating Japanese cedar
      pollinosis

<400> SEQUENCE: 47

Val His Pro Gln Asp Gly Asp Ala Lys Lys Trp Val Asn Gly Arg Glu
  1               5                   10                  15
```

POLYPEPTIDE

TECHNICAL FIELD

The present invention relates to a polypeptide having an antigenic epitope, which efficiently induces the production of an antibody specific to the antigenic epitope when permucosally administered even in the absence of an immunological adjuvant, a composition comprising the polypeptide, and use thereof, more particularly, to a polypeptide designed by linking a polypeptide comprising a B cell epitope of a protein as an antigen for the production of an antibody specific to the protein to a T cell epitope with a linker peptide comprising amino acid sequence of a protease recognition site, and further linking a peptide comprising an amino acid sequence of a cell attachment motif, which efficiently induces the production of an objective antibody, and a composition comprising the polypeptide, and use thereof.

BACKGROUND ART

In order to induce the production of an objective antibody specific to an antigen in living bodies, a purified antigen has been conventionally administered alone or along with an immunological adjuvant (which means a substance enhancing the immunological reaction specific to an antigen by non-specific stimulation of immune system) to living bodies. Such method has frequently used for preventing various infectious diseases, and been considered as the most effective method because it is also effective even in the case of treating antibiotic-resistant diseases such as diseases caused by viruses or toxins produced from microorganisms. Particularly, in such case, the method thought to be the only effective treatment because it enables to defend the living bodies from such diseases by inducing the production of objective antibodies specific to viruses and toxins. At present, the method is practically applied to produce vaccines including inactivated vaccines (inactivated microbes without infecting activity, which are prepared by treating with an organic solvent or irradiating UV) and attenuated vaccines (attenuated pathogens with a weak pathogenicity against living bodies). The almost vaccines (except polio vaccines) have been parenterally administered by injection. Some inactivated vaccines, however, have problems of significant affection to living bodies and less convenience because they require successive injection for several times to obtain sufficient antibody titer to attain a satisfactory biophylaxis.

While, live vaccines such as the attenuated vaccines have problems that they have a low preservation-stability and a possibility to become harmful virulent mutants after administered to affect living bodies. Both of the inactivated vaccines and the live vaccines must be concerned to be unsafe because they may give an anaphylactic shock to living bodies. Further, human serum albumin or gelatin has been conventionally used as a stabilizer and often added to vaccine preparations containing instable virus particles or huge sized proteins as immunogens to improve the stability of the vaccine preparations. However, such substances must be also concerned to be unsafe because they possibly bring unknown infectious microorganisms or anaphylactic shock. Most of the vaccine preparations have been produced for injection use. However, vaccine preparations have been required to be more stable and applicable without injection in order to be commercialized widely all over the developing countries where many people are dying of infectious diseases.

To solve the above problems, new type vaccines, having higher safeness and efficacy than conventional inactivated vaccines or live vaccines, has been eagerly studied all over the world by using a polypeptide comprising a partial amino acid sequence of an inactivated vaccine or live vaccine. Such new type vaccines are developed as B type hepatitis viral vaccines such as a recombinant vaccine and component vaccine. Peptides used as new type vaccines are usually desired to be a short fragment. However, excessively short fragments are difficult to be designed to have a broad major histocompatibility antigen (hereinafter, abbreviated as "MHC") class II restriction and satisfactory immunogenicity. While, in a view of enhancing immunogenicity of an objective antigen by permucosal administration, Lavelle, E. C. proposed in *Immunology*, Vol. 99, pp. 30-37, (2000) an immunizing method of an antigen with an immunological adjuvant such as cholera toxin (abbreviated as "CT", hereinafter), heat-instable type of enterotoxin from *E. coli*, or attenuated proteins thereof prepared by replacing a part of the amino acid sequence of CT or enterotoxin. The method enables to obtain a sufficient induction of the objective antibodies. However it has not been practical because it undesirably brings the induction of antibodies specific to CT and heat-instable type of enterotoxin from *E. coli* as immunological adjuvants.

Dental caries and periodontal diseases are considered as the two major diseases caused by microorganisms in dental field. Since such diseases are universal and less critical, they should be prevented and treated under the highest safeness. As examples of the methods for preventing dental caries, Japanese Patent Publication Kokai No. 122,633/94 discloses a passive immunizing method using an antibody obtained from an animal immunized with a peptide fragment of a tooth surface adhesive protein from *Streptococcus mutans*, and Japanese Patent Publication Kokai No. 511,422/02 discloses an anti-dental caries vaccine composed of a T cell epitope and a B cell epitope of glucan binding protein from *Streptococcus mutans*.

The present inventor had studied for the purpose of developing a short polypeptide which efficiently induces an antibody specific to cell surface protein antigen from *Streptococcus mutans* serotype C strain (It is abbreviated to "PAc", hereinafter.), which relates to early phase adhesion to the tooth surface, for many individuals having different MHC class II haplotype by permucosal administration even in the absence of immunological adjuvant. In the detail field, for the purpose of enhancing the production of antibodies capable of preventing dental caries, the inventor proposed to design the short polypeptide in the manner of linearly linking a T cell epitope having multiple restrictions from several MHC class II haplotypes to N-terminus of the partial amino acid sequence of PAc at the positions of 365 to 377 (SEQ ID NO:1) as a B cell epitope with a dipeptide linker such as a lysine-lysine sequence (Nishizawa. T., Imai, S., and Hanada, N., *Japanese Vaccine conference program abstract*, p. 77, (2000), Oishi Y. et al., *Oral Microbiology and Immunology*, Vol. 16, pp. 40-44, (2001)). However, even the polypeptide disclosed in the above reference does not have enough immunogenicity to induce the production of the antibody. Therefore, the above problems of conventional peptide vaccines have not still been solved. Japanese Patent Publication Kokai No. 504,118/96 discloses a synthesized peptide vaccine enabling to prevent infection of *Chlamydia trachomatis*, which designed by linking a B cell epitope to the carboxyl terminal side of a T cell epitope. However, the vaccine did not satisfactorily induce the production of the antibody when permucosally administered.

Under the above circumstance, the object of the present invention is to provide a peptide vaccine, which satisfactorily induces the production of an antibody in living bodies and safely applicable to living bodies even when permucosally administered.

DISCLOSURE OF THE INVENTION

The present inventor has studied a polypeptide enabling to more strongly induce the production of an antibody, which effectively prevents infection of dental caries causing microorganisms by a model system using a peptide fragment of PAc from *Streptococcus mutans* known as one of the microorganisms to solve the above problems.

The present invention is to provide a polypeptide designed by linking a cell attachment motif of cellular adhesive molecule to the peptide having a T-cell epitope at the amino terminal side of the linker peptide and a B-cell epitope at the carboxyl terminal side of the linker peptide to solve the above problems. As a result, the present inventor found that a polypeptide, which comprises (i) an amino acid sequence in the N-terminal region of a peptide, comprising a T cell epitope, restricted by MHC class II haplotypes in whole; (ii) another amino acid sequence comprising a B cell epitope for inducing antibody in the C-terminal region of the peptide, which is located in the peptide via an amino acid sequence, as a linker peptide, recognized by a protease, which is inserted between the two amino acid sequences (i) and (ii); and a peptide comprising an amino acid sequence(s) homologous to a cell attachment motif(s), which is linked to the peptide; and found that the polypeptide is one with a relatively high safeness, which sufficiently induces an antibody specific to the aimed antigen in terms of MHC class II haplotypes, less forms antibodies other than the aimed one, and dose not substantially induce side effects such as anaphylaxis when permucosally administered, for example, in an intranasal manner in the absence of immunological adjuvant.

The present invention provides a polypeptide designed by inserting a cell attachment motif of a cellular adhesive molecule to a peptide having a T cell epitope at the N-terminus of the linker peptide and B cell epitope at the C-terminus of the linker peptide to solve the above problems.

THE BEST MODE FOR CARRYING OUT THE INVENTION

The term "antibody" as referred to as in the present invention means immunoglobulin G (IgG), immunoglobulin M (IgM), and immunoglobulin A (IgA), and includes those secreted intranasally, orally, orbitally and intestinally as well as in the blood and the fluids body.

The B cell epitope sequence in the polypeptide of the present invention consists of an amino acid sequence of B cell epitope and optional other sequences to induce objective antibodies. It can be freely selected from B cell epitopes of various antigens such as toxins, allergens, enzymes, cell surface antigens, and tumor specific antigens from microorganisms, normal cells, and tumor cells. It also can be selected from antigenic epitopes disclosed literally or identified newly by a usual immunizing method using a partial peptide as long as it actually exerts antigenicity against living bodies. It can be selected from the same antigens having T cell epitopes (described below) used in the polypeptide of the present invention. In addition, it can be partially or wholly shared by the T cell epitopes. Therefore, any amino acid sequence having a B cell epitope can be freely selected from antigenic polypeptides, varying depending on the purposes of the objectively induced antibodies. Such purposes are examples of prevention of infection; prevention or treatment of cancers, tumors, ulcers, inflammatory diseases such as hepatitis, immunological diseases such as allergy and atopic dermatitis; neutralization of enzymes; and detection for various antigens used in a clinical test or the like. For example, the PAc peptide fragment described above (reported by Nishizawa. T., Imai, S., and Hanada, N., *Japanese Vaccine conference program abstract*, p. 77, (2000)) consists of an amino acid sequence of SEQ ID NO:1, and can be used for inducing antibodies capable of preventing dental caries. The part of B cell epitope sequence is usually composed of single B cell epitope. Desirably, such sequence can be in the form of a dimer, trimer or polymer by linking tandemly with one or more same or different B cell epitopes of the same antigen. In addition, the whole sequence of an antigen having a B cell epitope(s) can be used as the sequence. In order to enable the polypeptide of the present invention to treat a disease relating to some different antigenic proteins even in a single use, the polypeptide of the present invention can be designed to have a tandemly-linked multiple B cell epitopes chosen from the antigens. Such polypeptide is capable of inducing the multiple productions of antibodies. In such case, B cell epitopes in the polypeptide should be separated from each other with a linker peptide described below in order to be surely processed.

The T cell epitope sequence in the polypeptide of the present invention comprise any T cell epitope as long as it is restricted by an MHC class II haplotype of objective animals such as mammals including humans, fowls, reptiles and fishes, and presented as antigens for helper T cells. The T cell epitope sequence can be selected from the amino acid sequences literally disclosed as T cell epitopes. In addition, such T cell epitopes can be newly identified by a usual method, i.e., immunization with a partial peptide of an antigen, in order to use as a T cell epitope sequence of the polypeptide of the present invention. The T cell epitopes can also be selected from the same antigens to those of above-described B cell epitopes used in the polypeptide of the present invention. In addition, it can be partially or wholly shared by the B cell epitope. The T cell epitope sequence can be composed of a single T cell epitope or some of same or different T cell epitopes tandemly linked together. The T cell epitope sequence can exert its function even if the amino acid residues are substituted with other amino acid residues as long as agretopes (required for linking with MHC class II antigen) are conserved. Therefore, any amino acid sequence with conserved agretopes can be used as the T cell epitope sequence in the present invention. Multiagretope type polypeptide, which means a polypeptide having tandemly-arranged or overlapped agretopes restricted by multiple MHC class II haplotypes, can be more advantageously used as the T cell epitope part of the polypeptide because it enables the polypeptide to be applicable for many patients in order to defend person from infection, or prevent or treat allergic diseases. Many basic structures or agretopes restricted by MHC class II haplotype are disclosed literally. Based on such disclosures, the polypeptide comprising the T cell epitopes can be freely designed to have T cell epitopes suitable for its use. For example, the polypeptides having tandemly-arranged or overlapped T cell epitope or agretope sequences selected from that of different kinds of animals are acceptable to some different kinds of animals.

In addition, the B cell epitope sequence described above with the tandemly-arranged or overlapped B cell epitopes can be also used to induce some kinds of antibodies simultaneously.

If a polypeptide having only T cell epitope sequences and another polypeptide having only B cell epitope sequences are immunized without coupling each other, the production of objective antibodies is not efficiently enhanced. While, if the polypeptides is produced in a maner of simply couplig the B cell epitope sequence and the T cell epitope sequence, it possibly induces undesired antibodies recognizing a linking part with the desired antibodies simultaneously. Therefore, the polypeptide of the present invention is designed to inhibit the production of the antibodies recognizing the above amino acid sequence by inserting the linker peptide comprising the amino acid sequence of a protease recognition site for the purpose of allowing the polypeptide to be enzymatically divided into two polypeptides through the processing step of antigen presentation. Therefore, the polypeptide of the present invention has satisfactory immunogenicity, and enables to selectively enhance the production of objective antibodies specific to the B cell epitope sequence in a sufficient amount to exhibit the defending effect on living bodies without enhancing antibodies specific to the polypeptide.

The linker peptide used in the polypeptide of the present invention is inserted between the B cell epitope sequence and the T cell epitope sequence to couple them. Such linker peptides can be selected from protease recognition site sequences relating to antigen processing. Such sequences are examples of lysine-lysine (KK) dipeptide, lysine-arginine (KR) dipeptide and arginine-arginine (RR) dipeptide. Particularly, lysine-lysine dipeptide, which is a cathepsin B recognition site, is more desirable. If two polypeptides having a sequence overlapped T cell epitopes with B cell epitopes are linked together with a linker peptide, the resulting polypeptide enables to exert the both functions of T cell epitope and B cell epitope.

The cell attachment motif of cellular adhesive molecule used in the polypeptide of the present invention has a function to allow the polypeptide to stay on the surface of the mucosal cells for a long period. It can be selected from amino acid sequences of cell attachment motifs of cellular adhesive molecule including integrin family proteins or others. Examples of the amino acid sequences of integrin binding motif are arginine-glycine-asparagic acid (RGD: SEQ ID NO:2), arginine-glutamic acid-asparagic acid (RED: SEQ ID NO:3), leucine-asparagic acid-valine (LDV: SEQ ID NO:4), proline-histidine-serine-arginine-asparagine (PHSRN: SEQ ID NO:5), arginine-lysine-lysine (RKK: SEQ ID NO:6), and asparagic acid-glycine-glutamic acid-alanine (DGEA: SEQ ID NO:7) which are known as a cell attachment motif existing on cellular adhesive molecules such as fibronectin, collagen, vitronectin, fibrinogen, laminin, Tat protein of human immunodeficiency virus (abbreviated as "HIV", hereinafter). Examples of the amino acid sequences of the cell attachment motifs without belonging among integrin family are tyrosine-isoleucine-glycine-serine-arginine (YIGSR: SEQ ID NO:8), isoleucine-lysine-valine-alanine-valine (IKVAV: SEQ ID NO:9), arginine-phenylalanine-tyrosine-valine-valine-methionine-tryptophane-lysine (RFYVVMWK: SEQ ID NO:10), and isoleucine-arginine-valine-valine-methionine (IRVVM: SEQ ID NO:11). Particularly, RGD, RED, or YIGSR are desirable because they enhance the production of specific antibodies more strongly. The cell attachment motifs can be inserted at one or more positions selected from N- and C-terminus of the T cell epitope sequence and the B cell epitope sequence. They are preferably inserted into the polypeptide at N-terminus and/or C-terminus of T cell epitope sequence because of enabling to more strongly induce the production of antibodies specific to antigens having the B cell epitope sequence.

The method for producing the polypeptide of the present invention is not specifically restricted. The polypeptide can be prepared by a usual peptide synthesizing method. Optionally, the synthesized peptides can be linked each other according to The *Japanese Biochemical Societies Corporation, Sin-Seikagaku-Jikken-kouza* (New biochemical experimental Course), Vol. 1, "Tanpakushitsu (Protein) VI", pp. 3-44, (1992), published by Tokyo Kagaku Dojin Co., Ltd., Tokyo, Japan). The peptide can be synthesized using a peptide synthesizer commercialized by any manufacturers according to the attached protocols. The polypeptide can be also prepared according to conventional recombinant DNA techniques comprising the steps of; preparing a DNA coding for an amino acid sequence of the designed polypeptide; inserting the DNA into a self-replicable vector and introducing the resultant into a host, i.e., microbes such as *E. coli, Bacillus subtilis, Actinomycete*, and yeast, animals, plants, cells or tissues thereof; or generating the transgenic animals or plants; culturing or breeding the resultants; and collecting or purifying the polypeptide of the present invention by a usual method. Optionally, the polypeptide can be prepared by connecting the polypeptide with digestion sites of proteases other than that of digestion sites used for linking a T cell epitope sequence to a B cell epitope sequence, expressing the resulting polypeptide, and digesting the resulting polypeptides with the proteases. The microbes, animals, or plants having the expressed polypeptides of the present invention can be freely used intact as a composition comprising the polypeptide for oral use. The polypeptide can be directly prepared according to the above methods. In addition, It can be prepared by chemically binging the polypeptides prepared according to the above methods each other.

The polypeptide can be used alone or in combination with some polypeptides having the same B cell epitope. In order to simultaneously produce antibodies specific to several antigens, the polypeptides of the present invention can be freely used in combination with at least two of them having different B cell epitopes corresponding to each antigen. A composition comprising one or more pharmaceutically acceptable additives can be advantageously prepared as long as it does not affect the effect of the present invention. Examples of such additives are reducing or non-reducing saccharides such as glucose, maltose, trehalose, and sucrose; sugar alcohols such as sorbitol, mannitol, and maltitol; aqueous polymers such as agar, pullulan, guar gum, and gum arabic; proteins such as gelatin and silk, and hydrolysates thereof; effective ingredients of nutrition products with health promoting benefits, medical cosmetics, and pharmaceuticals such as lipids, amino acids, buffers, stabilizers, antimicrobials, and perfumeries; and immunological adjuvants such as alum and aluminum hydroxide. One or more of the above ingredients can be used alone or in combination. The form of the preparations comprising the polypeptide of the present invention is not restricted to a specific one as long as it is stably preserved for a long period. It can be freely selected from a solution, freeze-dried product, tablet, baccal, lozenge, powder, granule, cream, ointment, and syrup, varying depending on patient, administration, preservation, and transportation. The polypeptide of the present invention or the composition as above can be included in a liposome. It can be advantageously used in combination with an accelerator for facilitating the penetration into skins or tissues, and applied by iontophoresis to facilitate the penetration into the part with antigen presenting cells. Various foods and beverages such as a tablet candy, candy, and soft drink, which comprise the polypeptide of the present invention, can be orally intaken to allow the polypeptide to be absorbed permucosally. The polypeptide can be allowed to express in living bodies by gene therapy, i.e., direct administration of an RNA coding for the polypeptide of the present invention or by introduction of a DNA coding for the polypeptide to cells.

The polypeptide allows antibody productive animals such as mammals including humans, dogs, cats, or mice, fowls including chickens and ducks, reptiles, and fishes particularly hatchery fishes to produce antibodies to constitutive proteins or toxins which are inherent to or secreted from pathogenic virus, microbes, or bacteria. Therefore, the polypeptide effectively prevents or treats food poisonings caused by bacteria such as *bothulinum* and *E. coli* OH-157, and infectious diseases such as tetanus, diphtheria, and influenza. The polypeptide also effectively treats Alzheimer's disease which produces antibodies to amyloid β peptide, or it can be advantageously used in oral hyposensitization therapy for various allergy diseases or atopic dermatitis by predominantly producing specific IgG antibodies to allergens of mites, house dusts, pollens, foods, etc. The polypeptide of the present invention induces the production of IgA on mucosae and IgG in body fluids by permucosally administering into oral mucosae, nasal mucosae, orbital mucosae, guttural mucosae, vaginal mucosae, endotracheal mucosae, peritoneal mucosae, pleural mucosae, alveolar mucosae, esophagal mucosae, or alimentary mucosae such as gastric mucosae and intestinal mucosae. In addition, it can be administered subcutaneously, intracutaneously, or intramuscularly similarly in conventional vaccines, or in some cases it can be administered intravascularly. The polypeptide is useful for the production of specific antibodies to any proteins and intrinsically for antibody production against low-antigenic oligopeptides or polypeptides. Therefore, it can be advantageously used in such a manner of immunizing animals with synthesized oligopeptides for the purpose of producing antisera, and sensitizing immunocompetent cells in vitro as well as immunizing animal with synthesized oligopeptides for the purpose of producing monoclonal antibodies.

The polypeptide is also useful as an immunological adjuvant which induces the production of an antibody to be simultaneously administered with an antigen when administered to living bodies in combination with other antigen(s) or an antigenic protein deriving a B cell epitope of the polypeptide. Dose of the administration of the polypeptide is not restricted to a specific one as long as it sufficiently induces the production of an antibody to other antigen administered simultaneously or an antigen deriving the B cell epitope of the polypeptide. When the induction of the production of antibody to the polypeptide of the present invention is not desired, the dose of the polypeptide is usually 10% by weight or less, preferably, 1% by weight or less, more preferably, 0.1% by weight or less to the other antigen(s).

The administration method of the polypeptide of the present invention is not restricted to a specific one as long as it surely transports the polypeptide to the desired position. For example, it can be dropped on mucosae with a dropper or syringe, ingested orally, applied on mucosae after formed in a cream or gel form, introduced into the desired position with a catheter, sprayed after formed in a mist form with a spray or nebulizer, or aspirated into the nose, trachea, or lung. An administration method using a syringe, catheter, or intravenous drip can be used when the polypeptide is administered subcutaneously, intracutaneously, intramuscularly, intravascularly, and intracoelarly such as intraperitoneally and intrapleurally. Varying depending on the activity of inducing antibody, kind of disease, administration pathway, administration method, animal to be treated/prevented, a dose of the polypeptide of the present invention is usually 0.00001 to 100 mg/kg body weight, preferably, 0.0001 to 25 mg/kg body weight, more preferably, 0.001 to 10 mg/kg body weight.

The following experiments explain the polypeptide of the present invention in more detail.

EXPERIMENT

For the purpose of developing the polypeptide usable as a vaccine for defending living bodies from infectious disease, the following experiments were carried out to obtain vaccine polypeptides enabling to efficiently induce the production of antibodies in a permucosal administration using a model system of the production antibodies specific to PAc (a bacterial surface protein antigen as of tooth adhesive factors) of *Streptococcus mutans* serotype C strain (a kind of pathogen causing dental caries). The amino acid sequence of SEQ ID NO:1 in the following experiments is known to have cross-reactivity to PAc molecule and be minimum unit peptide antigen (It is described as "unit peptide" abbreviated to "UP", hereinafter) that induces only antibody having antidental caries activity (reported by Senpuku H., *Infection and Immunity*, Vol. 63, pp. 4695-4703). Polypeptides used in following experiments were synthesized by Fmoc method using a peptide synthesizer ("Model 350 Multiple Peptide Synthesizer" commercialized by Advanced Chemtech Corporation), and purified up to 95% or over by reverse phase HPLC using "TSK-GEL" a column sized 1 cm in diameter and 30 cm in length, commercialized by Tohso Co., Ltd., Tokyo, Japan.

Experiment 1

Analysis of Restriction of Mouse MHC Class II Haplotype Against UP

Five-week aged B10 congenic female mice, commercialized by Japan SLC Co. Ltd., Tokyo, Japan, were divided into eight groups consisting of five mice in view of difference of MHC class II haplotype. The all mice were intraperitoneally immunized with 200 μl/head of the UP and Freund's incomplete adjuvant (It is abbreviated as "FIA", hereinafter.), and boosted with them under the same condition after two weeks. All the mice were bled after one week. And then, the resulting antisera were subjected to measuring the titer against UP or PAc by a usual ELISA method using the UP or PAc as a coating antigen. The titers against the antigens are measured as follows; the antisera prepared of mice were serially diluted twofold and placed in microtiter plates to be subjected to measuring amount of antibodies by ELISA method using enzyme-labeled antibodies, and then, the resulting plates were subjected to measuring absorbance in 405 nm of each well using "MULTISCAN Bichromatech", a microtiter plate reader commercialized by Labosystem Corporation. The values of titers were calculated by averaging the maximum dilution values showing that the difference between the resulting values of well coated with the antigen and that of well uncoated one is 0.1 or over. The result is shown in Table 1. The parenthesized values followed each name of congenic mouse mean MHC class II haplotype.

TABLE 1

| Congenic mice | MHC class II haplotype | Titer against PAc | Titer against UP |
|---|---|---|---|
| B10.M | f | 19,112 | 35,391 |
| B10.D2 | d | 1,625 | 9,314 |
| B10.BR | k | 1,135 | 4,539 |
| B10.SM | v | 138 | 75 |
| B10.S | s | 138 | 75 |
| B10.Y | pa | 75 | 75 |
| B10.G | q | 75 | 45 |
| B10.RIII | r | 40 | 25 |

As evident from the result in Table 1, B10.M, B10.D2, and B10.BR congenic mice having MHC class II (H-2) haplotype f, d, and k, respectively, demonstrated that the production of specific antibody to UP and PAc is more strongly induced than other mice did (over about tenfold). Therefore, the UP was revealed to have effective B cell epitope capable of inducing specific antibodies and effective multiple T cell epitopes essential for antigen presentation on congenic mice having either MHC class II (H-2) haplotype of d, f or k. Since the UP is responsible to some mice having a different haplotype of MHC class II (H-2) in spite of a short peptide consisting of just 13 amino acid residues, it is considered to be a multiagretope type of T cell epitope. The result shows that the polypeptide of the present invention, even if being single and short, is possible to be artificially designed to sufficiently induce the production of antibodies in some individuals having a different haplotype of MHC class II.

Experiment 2

Confirmation of Multiagretope Type T Cell Epitope of Mouse

The above Experiment 1 confirmed presence of multiagretope type T cell epitope in the UP. Following experiment was carried out to confirm the location of functional amino acid. Valine substituted peptides were synthesized in the manner of exhaustively substituting any one of amino acid residue of UP with one valine residue, and subjected to immunizing the responsive mice to UP described above. As a result, the amino acid residues essential to induce the production of the antibodies in each mouse were deduced. Following, peptides substituted with valine residues were synthesized in the manner of substituting all of the deduced amino acid residues of UP with one valine residue, and subjected to immunizing according to the above. The resulting antisera were subjected to measuring their titers using ELISA. The agretopes of the UP responsible to each MHC class II haplotype were determined by analyzing the efficiency of the production of antibodies. The results are shown in Table 2 all together. The Table shows the only amino acids recognized by MHC class II haplotype.

TABLE 2

| | 1 | 2 | 3 | 4 | 5 | 6 | 7 | 8 | 9 | 10 | 11 | 12 | 13 |
|---|---|---|---|---|---|---|---|---|---|---|---|---|---|
| Amino Acid Sequence of UP | Thr | Tyr | Glu | Ala | Ala | Leu | Lys | Gln | Tyr | Glu | Aal | Asp | Leu |
| Amino Acid relating to restriction of B10.A(a) | | | | Ala | | | Lys | Gln | | | Ala | | |
| Amino Acid relating to restriction of B10.D2(d) | | | Glu | | | Leu | Lys | | | | | Asp | Leu |
| Amino Acid relating to restriction of B10.M(f) | | | | | | Leu | | | Tyr | Glu | | | Leu |
| Amino Acid relating to restriction of B10.BR(k) | Thr | Tyr | | | Ala | | | Gln | | | | | |

As evident from the result in Table 2, the polypeptide consisting of 13 amino acid residues has amino acid residues essential for recognition of MHC class II haplotype (agretope) in the overlapped or shifted form. The location of amino acid recognized by each MHC class II haplotype was confirmed as a multiagretope type T cell epitope in the UP.

Experiment 3

Design of Multiagretope Type Peptide Antigen

It is investigated whether remodeling the above UP by substituting their amino acids is possible to change immunological response relating to restriction of MHC class II haplotype in mice or not. The peptide having amino acid sequence of SEQ ID NO:12 (described as "YQTEL peptide", hereinafter), SEQ ID NO:13 (described as "YETDL peptide", hereinafter), and SEQ ID NO:14 (described as "YETAL peptide", hereinafter), which are designed by changing the part corresponding to agretopes of B10.D2(d) and B10.M(f) mouse (at the position of 10 to 12 of the amino acid sequence of SEQ ID NO:1) determined in Experiment 2, amino acid sequence of SEQ ID NO:1 (described as "YEADL peptide", hereinafter), SEQ ID NO:15 (described as "YEADLKQY peptide", hereinafter), which is designed by adding lysine-glutamine-tyrosine to the amino acid sequence of SEQ ID NO:1 at the carboxyl terminal, SEQ ID NO:17 (described as "UP-PAc(305-318)", hereinafter), which is designed by linking the peptide of SEQ ID NO:16 having the amino acid sequence at the positions of 305 to 318 from amino terminal of PAc known as a T cell epitope recognized by B10.S(s) mouse (described as "PAc(305-318), hereinafter") to amino terminal of UP, and SEQ ID NO:18 (described as "PAc(305-318)-UP", hereinafter), which is designed linking the UP and PAc(305-318) in reverse were synthesized and applied to B10 congenic mice to be immunized by the same method and schedule to Experiment 1. After two weeks from the boosting immunization, the antisera were prepared from the resulting blood samples, diluted with physiological saline 512-fold, and subjected to measuring the production of the antibodies by ELISA method according to Experiment 1. The production of antibodies in each congenic mouse was measured absorbance in 405 nm to be compared. The result was shown in Table 3. The result of measuring the production of antibodies specific to UP in mouse immunized with UP-PAc(305-318) and PAc(305-318)-UP were shown in Table 4. The antiserum presented 0.1 or more absorbance was judged to have antibody against UP in the diluted serum.

TABLE 3

| Congenic mouse | MHC class II haplotype | Titer against UP (Absorbance in 405 nm) YQTEL peptide | YETDL peptide | YETAL peptide | YEADL Peptide | YQADLKQY Peptide | PAc(305-318)-UP |
|---|---|---|---|---|---|---|---|
| B10.A | a | 0.01 | 0.01 | 0.01 | 0.28 | 0.29 | 0.29 |
| B10.D2 | d | 0.01 | 0.32 | 0.32 | 0.33 | 0.32 | 0.30 |
| B10.M | f | 0.01 | 0.12 | 0.33 | 0.32 | 0.32 | 0.32 |
| B10.BR | k | 0.22 | 0.31 | 0.30 | 0.30 | 0.30 | 0.30 |
| B10.S | s | 0.01 | 0.01 | 0.01 | 0.01 | 0.01 | 0.31 |
| B10.SM | v | 0.01 | 0.01 | 0.01 | 0.01 | 0.32 | 0.31 |

TABLE 4

| Congenic mouse | MHC class II haplotype | Titer Against The UP Immunizing with UP-PAc(305-318) | Immunizing with PAc(305-318)-UP |
|---|---|---|---|
| B10.D2 | d | 7,610 | 28,695 |
| B10.S | s | 106 | 108,205 |
| B10.M | f | 59,986 | 108,205 |

As evident from the result in Table 3, immunizing with YQTEL peptide artificially designed form UP induced the production of the antibody for only one B10.BR(k), while immunizing with YEADL peptide (UP) simultaneously induced the production of the antibody for three kinds of mice except of B10.S(s) and B10.SM(v). It is confirmed that changing one to three amino acids is effective to change the immunological responsibility for different individuals in view of MHC class II haplotype. YEADLKQY peptide, which is designed by adding lysine-glutamine-tyrosine to the UP, induced the production of antibody for four kinds of mice other than B10.S(s). Further, as evident from the results in Table 3 and 4, PAc(305-318)-UP which is designed by linking PAc(305-318) responded by B10.S(s) mouse irresponsible to the UP to the amino terminal of the UP, was confirmed to be a multiagretope type peptide antigen capable of inducing the production of the antibody for five kinds of mice including s type. Therefore, the above results revealed that artificially designing the polypeptide having the overlapping amino acid sequence restricted by each MHC class II haplotype based on the analysis of the amino acid sequence relating to more than one MHC class II haplotype restrictions on the antigen, enables to construct overlapping type of multiagretope type T cell epitope, which efficiently induces the production of the antibody to the antigen and is simultaneously restricted by more than one MHC class II haplotypes. The polypeptide designed by linking more than one T cell epitopes tandemly, so-called as "cluster type T cell epitope", is confirmed to be T cell epitope capable of efficiently inducing the production of the antibody as well as overlapping type epitope for individuals having more than one MHC class II haplotype restrictions. As evident from the result in Table 4, it is observed that the polypeptide designed by linking the UP to C-terminal side of PAc(305-318) more strongly induces the production of antibodies rather than the polypeptide designed by linking the UP to N-terminal side of PAc(305-318).

Experiment 4

Artificial Construction for Multiagretope Type Peptide Antigen for Human Use

Under the above result of experiment 3, in order to solve a problem of the individual difference due to MHC class II haplotype restriction, an overlapping multiagretope peptide (abbreviated as "OMP", in the following Experiments) having amino acid sequence of SEQ ID NO:19, which is responsible for more than one class II haplotypes, was constructed based on some preiously disclosed human restriction motifs of MHC class II haplotype (HLA-DR) against T cell epitopes. The peptide is capable of exerting for mouse the same function to human as T cell multiagretope (data not shown). Following Table 5 shows the amino acid recognized by each human MHC class II HLA-DR haplotypes.

TABLE 5

| | 1 | 2 | 3 | 4 | 5 | 6 | 7 | 8 | 9 | 10 |
|---|---|---|---|---|---|---|---|---|---|---|
| Amino Acid Sequence of OMP | Leu | Ala | Val | Tyr | Trp | Glu | Leu | Leu | Ala | Lys |
| Amino Acid relating to restriction of HLA-DR1 | | | | Tyr | | | Leu | | Ala | |
| Amino Acid relating to restriction of HLA-DR3 | | | Val | | | Glu | | | | |
| Amino Acid relating to restriction of HLA-DR4 | | | | | | | | | | |
| Amino Acid relating to | | | | | | | | | | |

TABLE 5-continued

| | | | | | | | | | | |
|---|---|---|---|---|---|---|---|---|---|---|
| restriction of HLA-DR5 | | | | | | | | | | |
| Amino Acid relating to restriction of HLA-DR6 | | | | | | | | | | |
| Amino Acid relating to restriction of HLA-DR7 | | | | Tyr | | | Leu | | | |
| Amino Acid relating to restriction of HLA-DR8 | | | | | | | | | | |
| Amino Acid relating to restriction of HLA-DR11 | | | | | Trp | | | Leu | | Lys |
| | 11 | 12 | 13 | 14 | 15 | 16 | 17 | 18 | 19 | 20 |
| Amino Acid Sequence of OMP | Tyr | Leu | Leu | Asp | Arg | Val | Gln | Lys | Val | Ala |
| Amino Acid relating to restriction of HLA-DR1 | | Leu | | | | | | | | |
| Amino Acid relating to restriction of HLA-DR3 | | | | | | | | | | |
| Amino Acid relating to restriction of HLA-DR4 | Tyr | | | Asp | | Val | Gln | | | |
| Amino Acid relating to restriction of HLA-DR5 | | | Leu | | Arg | Val | | Lys | | |
| Amino Acid relating to restriction of HLA-DR6 | | | Leu | | Arg | Val | | Lys | | Ala |
| Amino Acid relating to restriction of HLA-DR7 | | Leu | | | | | | | | |
| Amino Acid relating to restriction of HLA-DR8 | | | Leu | | | Val | | Lys | | |
| Amino Acid relating to restriction of HLA-DR11 | | | | | | | | | | |

Experiment 5

Influence of Linker Peptide for Enhancing the Production of Antibodies Specific to the Polypeptide The UP prepared in Experiment 3 does not have sufficient immunogenicity due to a too short peptide. In order to enhance its immunogenicity, tandemly linked polypeptides were tested. However, if the UPs were simply linked each other, the resulting peptides were concerned to have a new epitope sequence inducible of new antibodies at the linking part. For the purpose of allowing the only desired B cell epitope sequence to present, a linker peptide was arranged between the T cell epitope sequence and B cell epitope sequence. Such linker peptide is KK, which is previously disclosed as recognition site of endosome protease cathepsin B relating to the processing of antigen in antigen presenting cell. Following experiment is to confirm the influence of the linker peptide for enhancing the production of antibodies.

The polypeptides designed by inserting with KK between OMP and UP, represented by "OMP-KK-UP" having amino acid sequence of SEQ ID NO:20 and "UP-KK-OMP" having amino acid sequence of SEQ ID NO:21, respectively, were synthesized. The OMP was prepared in Experiment 4 and had a mouse T cell epitope, and the UP comprised a B cell epitope. They were immunized to BALB/c mice intraperitoneally by the method according to Experiment 1. The serum was prepared from mice and titers against OMP, the immunized polypeptide, and PAc were measured by the method according to Experiment 1. The result is shown in Table 6.

TABLE 6

| Polypeptide used as an antigen | Titer against PAc | Titer against the Immunized peptide | Titer against OMP |
|---|---|---|---|
| OMP-KK-UP | 836,462 | 782,685 | 1,731 |
| UP-KK-OMP | 961 | 29,921 | 1,211 |

As evident from the result in Table 6, OMP-KK-UP; arranging T cell epitope sequence at N-terminal region and B cell epitope sequence at C-terminal region and inserting a linker peptide between the two sequences; was revealed to efficiently induce the production of antibodies. This tendency was also observed in other strains of mice. Particularly, such tendency was remarkably observed in B10.S(s) mouse which PAc(305-318) was functional as a T cell epitope but UP was not so (referred to Table 4). It was revealed that the peptide at N-terminal side of the linker peptide is more effectively recognized as T cell epitope and the peptide at carboxyl terminal of the linker peptide is more effectively recognized as B cell epitope.

Experiment 6

Effect of a Cell Attachment Motif of Cell Adhesive Molecule on the Enhancement of Intranasal Immunogenicity of a Peptide Antigen A polypeptide having SEQ ID NO:22, arranged with two molecule of the UP, which has the amino acid sequence of SEQ ID NO:1 and induces the production of the antibodies having antidental caries activity, with the linker, lysine-lysine, (described as "di unit peptide" and abbreviated as "DUP", hereinafter) is so efficiently capable of enhancing the production of antibodies to need no immunological adjuvant in the case of injection use (subcutaneously or intraperitoneally). However, in the case of intranasal immunization, it is insufficient to use singly and actually needs an immunological adjuvant. In order to enhance the intranasal immunogenicity of the DUP, a cell attachment motif, which is possible to retain the DUP on mucosae for a long period, was introduced in the DUP. Such cell attachment motif was selected from integrin binding motifs of cell adhesion proteins such as fibronectin, laminin and collagen, which were determined to have a cell adhesion property. The following experiment was carried out to confirm the influence of the cell attachment motif on the immunogenicity. At first, the polypeptides having one or more cell attachment motif selected from RGD, RED, LDV, PHSRN, RKK, DGEA, YIGSR, IKVAV, IRVVM, and RFYVVMWK, at the N-terminal region were synthesized. As a negative control, DUP was prepared. As controls, polypeptides having DUP and either DRE (SEQ ID NO:23), DED (SEQ ID NO:24) or HAV (SEQ ID NO:25), which are amino acid sequences relating to cadherin without showing cell adhesion property in single use, were synthesized. Five week-aged female BALB/c mice, commercialized by Japan SLC, Inc., Shizuoka, Japan, were intranasally administered with 4 μl of phosphate buffer saline (hereinafter, abbreviated as "PBS") or distilled water containing 50 μg of each sterilized polypeptide in a manner of dropping by 2 μl into both nostrils. Mice of the negative control were administered with DUP alone. Mice of a positive control were administered with the DUP and 1 μl of CT. The DUP and the polypeptide having DUP and RGD were also intraperitoneally administered. After two weeks from the first immunization, the same polypeptide as a booster was administered again in the same manner. After two weeks from the second immunization, the same polypeptide as a booster was administered again in the same manner. After one week from the third immunization, sera were prepared from mice and subjected to measuring the titers of antubodies against PAc, DUP, CT and the polypeptide having the DUP and cell attachment motifs using the ELISA method according to Experiment 1. In order to confirm the effect of RGD or YIGSR sequence, a peptide fragment consisting of RGDS (SEQ ID NO:26) or YIGSR (SEQ ID NO:27) as an inhibitor against polypeptides having RGD or YIGSR sequence was applied together with the polypeptide to the mice in an excess amount to immunize the mice. The results are shown in Table 7. The mice immunized with the polypeptides having one or more motifs selected from RGD, RED, LDV, PHSRN, RKK, DGEA, YIGSR, IKVAV, IRVVM and RFYVVMWK showed the effect on the enhancement of the production of the antibodies specific to the UP. While, the mice immunized with the polypeptide having DRE, DED or HAV did not show such effect. The results of DUPs such as SEQ ID NO:27 ("RGD-DUP", hereinafter), SEQ ID NO:28 ("RED-DUP", hereinafter), SEQ ID NO:29 ("YIGSR-DUP", hereinafter), SEQ ID NO:30 ("DED-DUP", hereinafter) and SEQ ID NO:31 ("HAV-DUP", hereinafter) are typically shown in Table 7.

TABLE 7

| Polypeptide used as an antigen | Administration | Titer against PAc |
|---|---|---|
| DUP | Intranasal administration | 640 |
| CT + DUP | | 32,768 |
| RGD-DUP | | 5,069 |
| RGDS + RGD-DUP | | 256 |
| RED-DUP | | 1,395 |
| YIGSR-DUP | | 1,195 |
| YIGSR + YIGSR-DUP | | 235 |
| DED-DUP | | 544 |
| HAV-DUP | | 320 |
| DUP | Intraperitoneal administration | 312 |
| RGD-DUP | | 2,352 |

As evident from the result in Table 7, UP was not observed to induce the production of antibodies specific to the UP when intranasally administered in single use. While, the polypeptide having RGD or RED sequence as integrin attachment motif, or YIGSR as an attachment motif of laminin against laminin binding protein, i.e., RGD-DUP, RED-DUP, or YIGSR-DUP, was observed to have the effect on enhancing the production of antibodies. Adding an excess amount of RGDS or YIGSR peptide fragment, which is a short peptide as an inhibitor of binding to integrin, inhibited the production of antibodies specific to the PAc. The result suggested that cell attachment motif such as RGD and YIGSR is effective on more strongly inducing the production of antibodies, and the effect exerted by binding the DUP to integrins on cell surface of mucosae.

Experiment 7

Influence of Cellular Adhesive Molecule for Enhancement of the Production of Antibodies by Permucosally Administered Peptide Vaccine Following experiment is to investigate influence for enhancement of other peptide antigen by addition of integrin binding motif demonstrated in Experiment 6 and due to the position of the motif. Four kinds of the polypeptides; "RGD-OMP-KK-UP" (SEQ ID NO:32); "OMP-RGD-KK-UP" (SEQ ID NO:33); "OMP-KK-RGD-UP" (SEQ ID NO:34); "RGD-KK-UP-RGD" (SEQ ID NO:35) were synthesized in the manner of introducing RGD sequence into "OMP-KK-UP" at the positions of N-terminal or C-terminal side of the OMP or the UP; Wherein the RGD sequence was a kind of integrin binding motif and is suggested to enhance the production of antibodies specific to the polypeptide according to Experiment 6, and wherein the "OMP-KK-UP" was confirmed to be high enhancement of production of the specific antibody to PAc according to Experiment 5. As a positive control, CT is used, which is previously disclosed to have an adjuvant activity in permucosal administration. B10 mice were immunized with solutions containing each polypeptide with or without CT according to Experiment 6, and then, effects of each peptide on enhancing the production of antibodies were judged. The result is shown in Table 8.

TABLE 8

| Polypeptide used as an antibody | Titer against PAc | Titer against the immunized peptide | Titer against OMP |
|---|---|---|---|
| OMP-KK-UP | 32 | 128 | 32 |
| CT + OMP-KK-UP | 1,454 | 1,063 | 14 |
| RGD-OMP-KK-UP | 11,544 | 11,514 | 32 |
| OMP-RGD-KK-UP | 26,241 | 24,370 | 16 |
| OMP-KK-RGD-UP | 169 | 723 | 16 |
| OMP-KK-UP-RGD | 1,981 | 9,483 | 16 |

As evident from the result shown in Table 8, the insertion of RGD into OMP-KK-UP peptide enhanced the production of antibodies specific to PAc. Particularly, in the case of the inserting RGD at the position of N-terminal or C-terminal side of OMP, in other words, in N-terminal side from the linker, the polypeptide more remarkably enhanced the production of antibodies rather than the polypeptide having no RGD with CT. The almost of produced antibodies were capable of reacting to PAc. While, the polypeptides having RGD in C-terminal side from the linker induced many antibodies specific to the peptide including RGD sequence.

From above-described, the sequence of N-terminal side from the linker is recognized as T cell epitope, and the sequence of C-terminal side from the linker is recognized as B cell epitope in the presence of no adjuvant in intranasal immunization. The polypeptide efficiently enhances the production of antibodies specific to objective B cell epitope sequence. Particularly, it is revealed that the polypeptide having RGD sequence in N-terminal side from the linker is capable of inducing the antibodies specific to only PAc.

Experiment 8

Generality of Basic Design of Peptide Vaccine for Permucosal Administration

Following experiment is to investigate influence for the production of antibodies specific to B cell epitope sequence in the case of replacing T cell epitope or B cell epitope of the polypeptide constructed as RGD-(T cell epitope)-KK-(B cell epitope) according to Experiment 7 by placing other sequence instead of OMP or UP. The polypeptide represented by "RGD-OMP-KK-UP" (SEQ ID NO:38) or "T1-RGD-KK-UP" (SEQ ID NO:39) were designed and synthesized using T1 peptide (SEQ ID NO:36; which has been reported to be restricted to various MHC class II haplotypes and a multiagretope type T cell epitope derived from HIV IIIB gp120, reported by Ahlers J. D., *Proceedings of the National Academy of Sciences USA*, Vol. 94, No. 20, pp. 10856-10861, (1997)) as T cell epitope and OVA peptide fragment (hereinafter, abbreviated as "OVAp") consisting of 14 amino acid residues (SEQ ID NO:38; which is previously disclosed to induce the production of antibodies specific to ovalbumin, abbreviated as "OVA") for BALB/c mouse, reported by Hunt D. F., Science, Vol. 256, pp. 1817-1820, (1992). "OMP-KK-OVAp" (SEQ ID NO:40) and "T1-KK-UP" (SEQ ID NO:41) were prepared as controls. BALB/c mice were intranasally immunized with each above polypeptide according Experiment 6. The result is shown in Table 9.

TABLE 9

| Polypeptide used as an antibody | Titer against OMP | Titer against the immunized peptide | Titer against OVA | Titer against CT |
|---|---|---|---|---|
| OMP-KK-OVAp | 108 | 1,589 | 1,656 | — |
| RGD-OMP-KK-OVAp | 235 | 5,080 | 11,692 | — |
| CT + OMP-KK-OVAp | 7,319 | 21,310 | 25,654 | 3,656,835 |
| **Polypeptide used as an antibody** | **Titer against T1** | **Titer against the immunized peptide** | **Titer against Pac** | **Titer against CT** |
| T1-KK-UP | 103 | 160 | 320 | — |
| T1-RGD-KK-UP | 107 | 1,707 | 1,579 | — |
| CT + T1-KK-UP | 69 | 1,152 | 176 | 139,264 |

*"—": Not tested

As shown in Table 9, the mice immunized intranasally with RGD-OMP-KK-OVAp or T1-RGD-KK-UP showed a remarkable enhancement of the production of antibodies specific to OVA or PAc. It is confirmed that insertion of RGD sequence imparted the polypeptide to more strongly enhance the production of antibodies than polypeptides having no RGD sequence.

Experiment 9

Effect of the Polypeptide of the Present Invention on Enhancement of the Production of Antibodies Specific to Other Antigen CT, usually used as an adjuvant, is known to strongly induce antibodies specific to not only CT but also other antigens when permucosally administered together with the other antigens. Otherwise, the polypeptide of the present invention such as RGD-OMP-KK-UP, OMP-RGD-KK-UP, RGD-OMP-KK-OVAp, and T1-RGD-KK-UP induced specific antibodies even without CT. Following experiment is to investigate whether the polypeptide enhances the production of antibodies specific to other antigens or not.

Influence of Various Polypeptides for the Production of Antibodies Specific to Bovine Serum Albumin in Intranasal Administration BALB/c mice were immunized with a physiological saline solution containing 4 μg of bovine serum albumin (hereinafter, abbreviated as "BSA") and either of 1 μl of DUP, RGD-DUP, OMP-KK-UP, OMP-RGD-KK-UP, OMP-KK-OVAp or RGD-OMP-KK-OVAp, or 2 μg of CT in intranasal administration according to Experiment 6, and titers in the blood were measured. The result is shown in Table 10. Titers of antibodies against BSA, co-administered peptides, and CT were measured.

Influence of Various Polypeptides for Antibody Production Against Ovalbumin in Intranasal Administration B10.D2 or BALB/c mice were immunized with a physiological saline solution containing 4 μg of OVA and either of 1 μg of OMP-RGD-KK-UP, OMP-RGD-KK-OVAp, or 2 μg of CT in intranasal administration according to Experiment 6, and then, titers in the blood were measured. The result is shown in Table 10. Titers of antibodies against OVA, OMP-RGD-KK-OVAp, and CT were measured.

TABLE 10

| Polypeptide used as an antibody | Titer against CT | Titer against BSA | Titer against the immunized peptide |
|---|---|---|---|
| BSA | — | 32 | — |
| CT + BSA | 1,887,437 | 838,861 | |
| DUP + BSA | — | 179 | 83 |
| RGD-DUP + BSA | | 6,912 | 154 |
| RGDS + RGD-DUP + BSA | | 576 | 128 |
| OMP-KK-UP + BSA | | 20,480 | 1,152 |
| OMP-RGD-KK-UP + BSA | | 109,227 | 213 |
| OMP-KK-OVAp + BSA | | 1,441,792 | 224 |
| RGD-OMP-KK-OVAp + BSA | | 1,527,887 | 256 |

TABLE 10-continued

| Polypeptide used as an antibody | | Titer against CT | Titer against OVA | Titer against the immunized peptide |
|---|---|---|---|---|
| B10.D2 | OVA | — | 203 | — |
| mouse | CT + OVA | 681,574 | 24,576 | |
| | OMP-RGD-KK-UP + OVA | — | 10,242 | 24 |
| BALB/C | OVA | | 16 | — |
| mouse | CT + OVA | 524,288 | 4,096 | |
| | OMP-RGD-KK-UP + OVA | — | 2,176 | 26 |

*"—": Not tested

As shown in Table 10, antibodies specific to BSA or OVA were hardly induced in the blood of the mice when intranasally administering BSA or OVA alone. In contrast, mice immunized with BSA or OVA in combination with OMP-RGD-KK-UP, OMP-KK-OVAp or RGD-OMP-KK-OVAp showed a strong enhancement of the production of antibodies specific to BSA or OVA. In addition, mice immunized with BSA in combination with RGD-DUP or OMP-KK-UP showed the production of antibodies specific to BSA than. However, latter mice showed lower enhancement than former mice. Mice immunized with BSA or OVA in combination with CT showed the same degree of the production to the above mice. Mice immunized in combination with 1 μg of OMP-RGD-KK-UP, OMP-KK-OVAp, or RGD-OMP-KK-OVAp showed a slight production of antibodies specific to the peptide, in contrast, mice immunized in combination with 2 μg of CT showed strongly enhancement of the production of antibodies specific to CT. Therefore, OMP-RGD-KK-UP, OMP-KK-OVAp, or RGD-OMP-KK-OVAp is confirmed to be useful for inducing antibodies specific to other antigens as an immunological adjuvant in the manner of using them in an insufficient or small amount to be induce the production of their antibodies.

As described above, it is confirmed that cell attachment motifs are allowed the polypeptide consisting of B cell epitope connected to T cell epitope with protease recognition site such as KK to enhance antibody production against B cell epitope. The polypeptide of the present invention is useful as inducers for specific antibody production or enhancer for antibody production because it is efficiently capable of inducing antibody production against B cell epitope peptide in the polypeptide except inducing useless antibody production against other site than B cell epitope even when administered without immunological adjuvant intranasally. As the result that living bodies administered with the polypeptide efficiently produce antibody against antigenic protein deriving the B cell epitope used for immunizing, the polypeptide of the present invention is capable of inducing various antibody such as antibody for preventing infectious, antibody for neutralizing toxin or enzyme active center, and antibody against allergen in the presence of no immunological adjuvant in mucosal immunization including nasal immunization. The polypeptide is useful as peptide vaccine for intranasally immunizing in order to prevent infection. The polypeptide effects immunological adjuvant when administered with other antigen together.

The following examples explain the polypeptide of the present invention concretely, but the present invention must not be restricted by these examples.

EXAMPLE 1

Composition for Enhancing the Production of Antibodies Specific to PAc

The syrup agent containing the polypeptide prepared in Experiment 7 was obtained by dissolving 100 μg/ml of any one of RGD-OMP-KK-UP, RGD-OMP-KK-UP, RGD-OMP-KK-UP, or OMP-KK-UP, and 40% of α,α-trehalose (reagent grade, commercialized by Hayashibara Biochemical Laboratories, Inc., Okayama, Japan) in distilled water, sterilizing by a usual method. The resulting syrup was placed by 2 ml into sterilized vials, and sealed. Since the product is stable and restricted by various MHC class II haplotypes, it exerts the effect of vaccine which enhances to produce the antibody having the effect on preventing dental caries. The product can also be useful as immunological adjuvant which enhances the antibody against other antigen when permucosally and intracutaneously administered with the polypeptide together.

EXAMPLE 2

Composition for Enhancing the Production of Antibodies Specific to PAc

Agent containing the polypeptide prepared in Experiment 7 was obtained by dissolving 10 μg/ml, 100 μg/ml or 1,000 μg/ml of RGD-T1-KK-UP in physiological saline containing 1% (w/v) of sucrose, and sterilizing by filtration. The resulting solution was placed by 1 ml into sterilized vials, freeze-dried, and sealed in a usual manner. The product is a preparation for permucosal administration or infection, which is stable and has a satisfactory effect on preventing dental caries. The product is used after dissolved in 1 ml of distilled water for injection. Since the product is stable and restricted by various MHC class II haplotypes, it exerts the effect of vaccine, which efficiently enhances the production of the antibodies having the effect on the prevention of dental caries, in intranasal or oral administration for many human or animals. The product can also be useful as an immunological adjuvant which enhances the production of other antibodies specific to other antigens when permucosally and intracutaneously administered together with the other antigens.

EXAMPLE 3

Toxicity Test for Composition Containing the Polypeptide $LD_{50}$ of the preparation containing the polypeptide, prepared in Example 1 or 2, was investigated by administering five week-aged DDY male mice with the physiological saline containing 12.5 mg/ml of any one of the polypeptides and 0.5% of sucrose orally, intraperitoneally, or intramuscularly according to a usual method. As a result, both of the $LD_{50}$ of the preparations were 100 mg (peptide weight)/kg mouse body weight or over. Therefore, the preparations are considered as safe preparations with no toxicity when administered to humans or animals.

EXAMPLE 4

Composition for Enhancing the Production of Antibodies Specific to HIV

Any one of OMP, T1, gag protein at the position of 298-312 (SEQ ID NO:42) and pol protein at the position of 596-610 (SEQ ID NO:43) was selected as a T cell epitope sequence. The gag protein and pol protein were reported as T cell epitopes restricted by HLA-DR1-9 or 51-53, by Wilson, C. C., *Journal of Virology*, Vol. 75, pp. 4195-4207, (2001). The polypeptides of the present invention were designed in a manner of arranging RGD sequence at N-terminal or C-terminal region of either of the T cell epitope sequences, and then, arranging B cell epitope sequence of V3 loop peptide of gp120 protein from HIV (SEQ ID NO:44), reported by Haynes, B. F., The Journal of Immunology, Vol. 151, pp. 1646-1653, (1993), at the C-terminal region of the resulting sequence, which positions via KK linker inserted between the two sequences. 150 μg/ml of the one or two of the above polypeptides and 100 mg/ml of mannitol were dissolved in physiological saline. The resulting solutions were placed by 1 ml in 5 ml-volume vials and freeze-dried. The product is useful as a vaccine for inhibiting the spreading of HIV and delaying the development of HIV because it is capable of efficiently enhancing the production of antibodies specific to HIV in permucosal or percutaneous administration. In addition, it enables to target for variety person because of restricted to various MHC class II haplotypes. The product is also useful as immunological adjuvant for enhancing the production of other antibodies specific to other antigens which is permucosally administered together with the other antigens.

EXAMPLE 5

Composition for Enhancing Antibody Production Against Influenza Virus

The polypeptides of the present invention were designed in a manner of arranging RGD or YIGSR sequence at N-terminal or C-terminal region of the T cell epitope sequence selected from OMP, T1, SEQ ID NO:42 and 43, and then, in order to induce neutralizing antibodies against an influenza virus, arranging B cell epitope sequence of HA (hemaggrutinin) protein at the position of 91-108 from influenza virus (SEQ ID NO:45) reported by Ben-Yedidia T., *Molecular Immunology*, Vol. 39, pp. 323-331, (2002) at the C-terminal region of the resulting sequence, which positions via KK linker inserted between the two sequences. Each 75 μg/mL of one or more the above peptides was admixed with physiological saline containing 0.5 mg/ml of human albumin. The resulting solutions were placed by 1 ml in 5 ml-volume vials and freeze-dried in a usual manner. The product is useful as a vaccine for inhibiting the infection of influenza virus because it is capable of efficiently enhancing the production of the antibodies specific to influenza virus in permucosal or percutaneous administration. In addition, it is enabling to target for variety person because of restricted to various MHC class II haplotypes. The product is also useful as immunological adjuvant for enhancing the production of other antibodies specific to other antigens, when applied together with the other antigens in permucosal administration.

EXAMPLE 6

Papilloma Virus Vaccine

The polypeptides of the present invention were designed in a manner of arranging RGD sequence at N-terminal or C-terminal region of the T cell epitope sequence selected from OMP, T1, SEQ ID NO:42 and 43, and then, in order to induce neutralizing antibodies against human papilloma virus, arranging B cell epitope sequence of L2 protein (SEQ ID NO:45) from human papilloma (SEQ ID NO:46), reported by Kawana K., Vaccine, Vol. 19, pp. 1496-1502, (2001), at the C-terminal region of the resulting sequence, which positions via KK linker inserted between the two sequences. Each 200 μg/ml of one or more the above peptides was admixed with phosphate buffer saline containing 0.25 mg/ml of gelatin. The resulting solution was placed by 0.5 ml in 5 ml-volume vials and freeze-dried in a usual manner. The product is useful as a vaccine for inhibiting the infection of human papilloma virus because it is capable of efficiently enhancing the production of antibodies specific to human papilloma virus in permucosal or percutaneous administration. In addition, it enables to target for variety person because of restricted to various MHC class II haplotypes. The product is also useful as immunological adjuvant for enhancing the production of other antibodies specific to other antigens when applied together with the other antigens in permucosal administration.

EXAMPLE 7

Composition for the Production of Antibodies Specific to OVA

100 μg/ml of RGD-OMP-KK-OVAp prepared in Experiment 8 was dissolved with 40% of α,α-trehalose (reagent grade, commercialized by Hayashibara Biochemical Laboratories, Inc., Okayama, Japan) in distilled water and sterilized in a usual manner. The resulting syrup was placed by 2 ml in sterilized vials, and sealed to obtain a syrupy vaccine containing the polypeptide. The product is satisfactorily stable, and efficiently enhances the production of the antibodies specific to OVA when intranasally, orally or percutaneously administered to animals. The product can also be useful as immunological adjuvant which enhances the antibody against other antigen when intranasally administered with the polypeptide together.

EXAMPLE 8

Composition for Enhancing the Effect of Influenza Vaccine on the Production of Antibodies 4 μg of either commercialized influenza HA vaccine by Astellas Pharma Inc., Tokyo, Japan, or virus surface antigenic protein such as HA and M protein was dissolved with 1 μg of either RGD-OMP-KK-OVAp or RGD-OMP-KK-UP in 1 ml of physiological saline. The resulting solutions were placed by 0.5 ml in sterilized vials and sealed to obtain pharmaceutical preparations. The product containing the usual influenza vaccine or the viral surface antigenic protein, which dose not induce by permucosal administration in single use, strongly induces the production of antibodies specific to the viral surface antigenic protein due to the immunological adjuvant-like action of RGD-OMP-KK-OVAp or RGD-OMP-KK-UP. The product can be used as a vaccine, which strongly induces the production of the antibody having an activity for preventing the infection of influenza virus when intranasally administered three or four times at two weeks interval.

EXAMPLE 9

Oral Composition for Hyposensitization of Japanese Cedar Pollinosis

The polypeptides of the present invention were designed in a manner of arranging RGD sequence at N-terminal or C-terminal region of the T cell epitope sequence selected from OMP, T1, SEQ ID NO:42 and 43, and then, in order to induce the production of antibodies specific to Japanese cedar pollen allergens, arranging B cell epitope sequences "VHPQDGDA" of Cry j 1, reported by Kawana K., Vaccine, Vol. 19, pp. 1496-1502, (2001) and "KWVNGRI" of Cry j 2, reported by Tamura Y., Clinical and Experimental Allergy, Vol. 33, No. 2, pp. 211-217, (2003), at the C-terminal region of the resulting sequence, which positions via KK linker inserted between the two sequences to obtain the polypeptide consisting of the amino acid sequence of SEQ ID NO:47. Each 200 μg/ml of one or more the above peptides was admixed with phosphate buffer saline containing 0.25 mg/ml of gelatin to obtain an oral composition for hyposensitization of Japanese cedar pollinosis. The product is useful as a preparation for hyposensitization of Japanese cedar pollinosis because it is capable of efficiently enhancing the production of IgG antibodies specific to Cry j 1 and Cry j 2 in permucosal or percutaneous administration. In addition, it enables to target for variety person because of restricted to various MHC class II haplotypes.

INDUCTRIAL APPLICABILITY

As described above, the present invention relates to the polypeptide containing a special antigen peptide, which enables to enhance the production of an antibody specific to antigenic epitope of an objective antigen or a composition thereof without immunological adjuvant. The polypeptide of the present invention is useful as vaccine in use for many person as well as antibody productive animals such as mammals, fowls, reptiles, and fishes, or as antigen for enhancement of specific antibody production because it is capable of using in permucosal administration such as intranasal and oral administration more easy and safe than percutaneous injection and is restricted in varieties of MHC class II haplotypes. It is also useful as immunological adjuvant for enhancing the production of antibodies specific to other antigens when administered together with the other antigens.

The invention claimed is:

1. A polypeptide, consisting of the amino acid sequence of SEQ ID NO:32, SEQ ID NO:33 or SEQ ID NO:39.

2. A composition comprising the polypeptide of claim 1 and a pharmaceutically acceptable additive.

* * * * *